United States Patent [19]

Strohmaier

[11] 4,222,738

[45] Sep. 16, 1980

[54] DENTAL HANDPIECE AND DRIVE ARRANGEMENT THEREFOR

[75] Inventor: Ernst Strohmaier, Schussenried, Fed. Rep. of Germany

[73] Assignee: Kaltenbach & Voigt GmbH & Co., Biberach an der Riss, Fed. Rep. of Germany

[21] Appl. No.: 810,991

[22] Filed: Jun. 29, 1977

[30] Foreign Application Priority Data

Apr. 18, 1977 [DE] Fed. Rep. of Germany ....... 2717013

[51] Int. Cl.³ .............................................. A61C 1/10
[52] U.S. Cl. ..................................... 433/105; 433/114
[58] Field of Search ................. 32/26; 74/750 R, 785; 192/48.91; 433/114, 105

[56] References Cited

U.S. PATENT DOCUMENTS

| 663,089 | 12/1900 | Mitchell | 32/26 |
| 3,050,321 | 8/1962 | Howe et al. | 192/67 R |
| 3,115,791 | 12/1963 | Dean | 74/750 R |
| 3,292,459 | 12/1966 | Krzyszczuk | 74/785 |
| 3,436,980 | 4/1969 | Loge et al. | 74/352 |
| 3,566,471 | 3/1971 | Bull | 74/785 |
| 3,942,392 | 3/1976 | Page, Jr. et al. | 74/750 R |
| 3,999,642 | 12/1976 | Johnson | 192/48.91 |
| 4,121,342 | 10/1978 | Flatland | 32/26 |

FOREIGN PATENT DOCUMENTS 276939 8/1927 United Kingdom ....................... 32/26

*Primary Examiner*—Louis G. Mancene
*Assistant Examiner*—John J. Wilson
*Attorney, Agent, or Firm*—J. Harold Nissen

[57] ABSTRACT

A dental handpiece having a drive arrangement which provides for different speeds to be imparted to a dental tool. The drive arrangement comprises a planetary gear arrangement and a transmission member adapted for intercoupling to provide the different speeds at an output drive shaft for the dental tool. Interengagement means comprising axial slots are provided on the planetary gear arrangement, and a counter-engagement means including balls having segments which protrude from the transmission are provided to engage the interengagement axial slots to transmit the different speeds from a drive motor to the dental tool.

5 Claims, 9 Drawing Figures

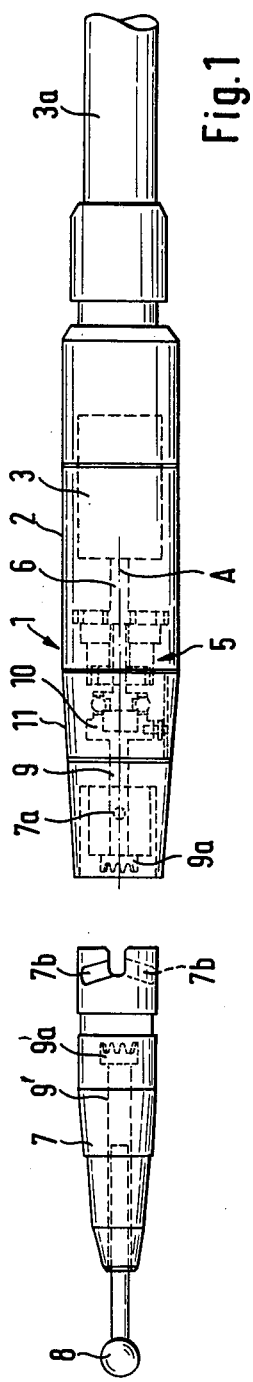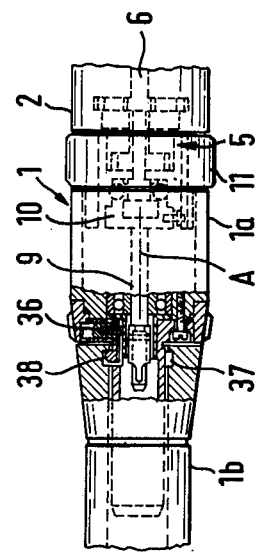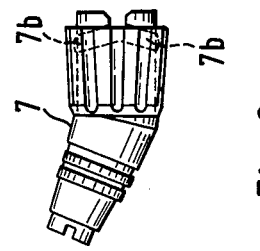

DENTAL HANDPIECE AND DRIVE ARRANGEMENT THEREFOR

BACKGROUND OF THE INVENTION

This invention relates to a drive arrangement for a dental handpiece in order to drive a dental tool at different speeds.

More particularly, the invention is concerned with a straight or angular dentists' handpiece having an elongated handpiece sleeve having a drive motor arranged therein. The shaft of the drive motor drives or is connected with the input shaft of a planetary gear in order to drive a tooth treatment tool which can be inserted in the tip of the handpiece. Since it is necessary for the dentist to drive the tool at different speeds, it is necessary to provide for speed adjustments or variations. For this purpose, a transmission member is provided to transmit different speeds to the dental tool. The transmission member can be brought into engagement with the planetary gear in different transmission ratios. In order to establish different transmission ratios, the transmission along an axis is displaceable parallel to the axis of the handpiece sleeve by means of an external shift member on the handpiece.

DESCRIPTION OF THE PRIOR ART

A similar handpiece, but one which has no transmission member of the above-mentioned type, and therefore, no shift member, is known through W. German Utility Model DT-GM 1,992,122. This utility model is concerned with a dental handpiece in which the handpiece sleeve is transversely divided into two parts. One part is an actual handpiece portion which is used to receive the tooth treatment tool, and the second part is a motor portion comprising the motor. The motor is designed as a fluid flow motor, and the shaft of the motor is provided at its free end with a first engagement means. At a radial distance from the free end and the first engagement means, a second or additional engagement means is provided at a cage type epicyclic rotary body rotating about the shaft of the motor. This epicyclic body is driven by the outer circumference of the motor shaft by means of balls constituting a frictional drive, and running along a non-rotation hollow rim. In this way, two different speeds can be obtained. One speed is obtained at a transmission ratio 1:1 from the first engagement means at the motor shaft, and a second speed is obtained at a step-down ratio from the second or additional engagement means of the rotary body.

The dental handpiece made in accordance with DT-GM 1,992,122 is quite complicated and time consuming in order to accomplish a change of speed. It should be noted that with this embodiment, two different handpiece parts are required, which are provided with special counter-engagement means corresponding to the two radially spaced engagement means of the motor shaft. The two different handpiece parts which are required, of course, represent increased cost. Besides, the necessity to exchange the handpiece parts necessary for each change of speed is so complex that its use becomes cumbersome.

Another handpiece similar to the above-mentioned kind is known from U.S. Pat. No. 3,436,980. However, this known handpiece does not have a planetary gear, but a special gear shift transmission which is designed as an intermediate gear transmission with three intermediate gears displaceable in radial guideways. The three intermediate gears each consist of a countershaft with a gear wheel at each shaft end. By means of a shift member, one of the three intermediate gears can be brought into engagement counter to the pressure of springs with the input shaft and the output shaft of the transmission. This will provide for three different transmission or speed ratios. The gear construction required for this is relatively complicated and trouble prone. Besides, the countershafts and their radial guideways require a large volume of space, so that the handpiece becomes relatively large and cumbersome.

Another handpiece similar to the above is known from U.S. Pat. No. 3,942,392. In this handpiece, the transmission member is formed from an epicyclic carrier of a gear type planetary gear. This handpiece can provide two different speeds. A major wheel of the gear train which is adapted for engagement with the carrier is formed as a hollow rim having teeth. During the relative displacement between the epicyclic carrier and the major wheel along an axis parallel to the axis of the handpiece, the teeth of the epicyclic wheels carried by the epicyclic carrier get into and out of engagement with the teeth of the major wheel, depending on the direction of displacement. Due to the fact that when shifting from one speed to the other two parts which form part of the gear train are displaceable relatively to each other, special problems arise as a result of bearing problems. Because of the bearing problems, a complicated construction of the gear train is necessary, and the gear parts which move into and out of engagement tend to be trouble-prone.

An object of the invention is to provide a dental handpiece having a planetary gear arrangement which is simple and compact.

Another object of the invention is to provide a dental handpiece having a planetary gear arrangement with no displaceable parts and which can be shifted from one speed to another easily and rapidly.

SUMMARY OF THE INVENTION

To solve this problem it is proposed according to the invention that the interengaging gear portions of the planetary gear are axially and radially immobile. Accordingly, the input shaft to the planetary gear, the central roll body of the planetary gear secured on the input shaft, the epicyclic roll bodies in engagement with the central roll body, the epicyclic carrier guiding the epicyclic roll bodies, and the major wheel in engagement with the epicyclic roll bodies, are all arranged axially and radially immobile with respect to each other and with reference to the axis of the handpiece sleeve. The epicyclic carrier as well as the input shaft of the planetary gear are provided in the region of the end towards the drive shaft and are provided with engagement means which are spaced from each other axially and radially and which are selectively engageable with counter-engagement means of the transmission member. In addition, the transmission member is arranged nonrotationally on the drive shaft, but it is axially displaceable with the counter-engagement means so that they can engage the engagement means in each position.

With this design, the special transmission member is not rotatable with respect to its own shaft, but it is axially displaceable with respect to its own or the drive shaft. Furthermore, the special transmission member while it is not rotatable with respect to its own shaft, is rotatable together with its own drive shaft and is keyed thereto by means of a cross pin. And, the special transmission while it is not rotatable relative to its own drive shaft, it is axially displaceable along its own drive shaft. The drive shaft is used to drive the tooth treatment tool, e.g. a drill. The construction and the shifting of the gear from one speed to the other is therefore simple and uncomplicated. The planetary gear may be a ball planetary gear for instance in the manner and type of DT-GM 1,992,122 or a gear type planetary gear.

The engagement means associated with the input shaft and the epicyclic carrier cooperate with the counter-engagement means on the transmission member to provide for two different speed transmission engagements. One of the engagement means is located on the inner wall of an output stub forming part of the epicyclic carrier and points toward the drive shaft and the other is on the input shaft. These engagement means are in the form of axial grooves distributed over the circumference of the carrier inwardly thereof and on the input shaft. The engagement means on the transmission member comprise members which are provided with elevations emerging from both sides of the circumferential wall of the transmission member.

The transmission member is in the form of an open pot with its openings facing the input shaft and the epicyclic carrier. The wall of the transmission member is generally cylindrical in shape and has a wall thickness which is less than the thickness of members contained therein which carry the counter-engagement means. The portions of the members which form the counter-engagement means are adapted to engage within the axial grooves on the input shaft or the inner wall of the epicyclic carrier depending upon the speed transmission desired, which is controlled by the displacement position of the transmission member. Expediently the elevations forming the counter-engagement means are formed by protruding segments of balls inserted in the cylindrical circumferential wall of the transmission member.

One of the advantages of the arrangement of the transmission member being non-rotational on the drive shaft but axially displaceable therealong consists in that the open pot type transmission member has a hollow trunnion type extension surrounding the drive shaft. The trunnion type extension has a continuous axial slot which terminates prior to its free end on the drive shaft. The cross-pin traverses the drive shaft and is received in the axial slot. The axial slot forms an oblong hole, and the longitudinal median plane of the oblong hole passes through the axis of the hollow trunnion type extension so that axial movement along the drive shaft is axially guided.

Other objects, advantages and the nature of the invention will become readily apparent from the following description used to illustrate the preferred embodiments of the invention as described in connection with the accompanying drawings.

BRIEF DESCRIPTION OF THE DRAWINGS

FIG. 1 illustrates a dental handpiece together with a straight tip. The dental handpiece and tip are separated from each other. The drive motor, the planetary drive and drive shaft are shown in lateral elevation in dashed lines, all enclosed within the dental handpiece.

FIG. 2 shows an angular tip in lateral elevation. The angular tip can be substituted for the straight tip shown in FIG. 1.

FIG. 3 is a detail of a modification of the dental handpiece of FIG. 1.

DESCRIPTION OF THE PREFERRED EMBODIMENTS

Figure 4:
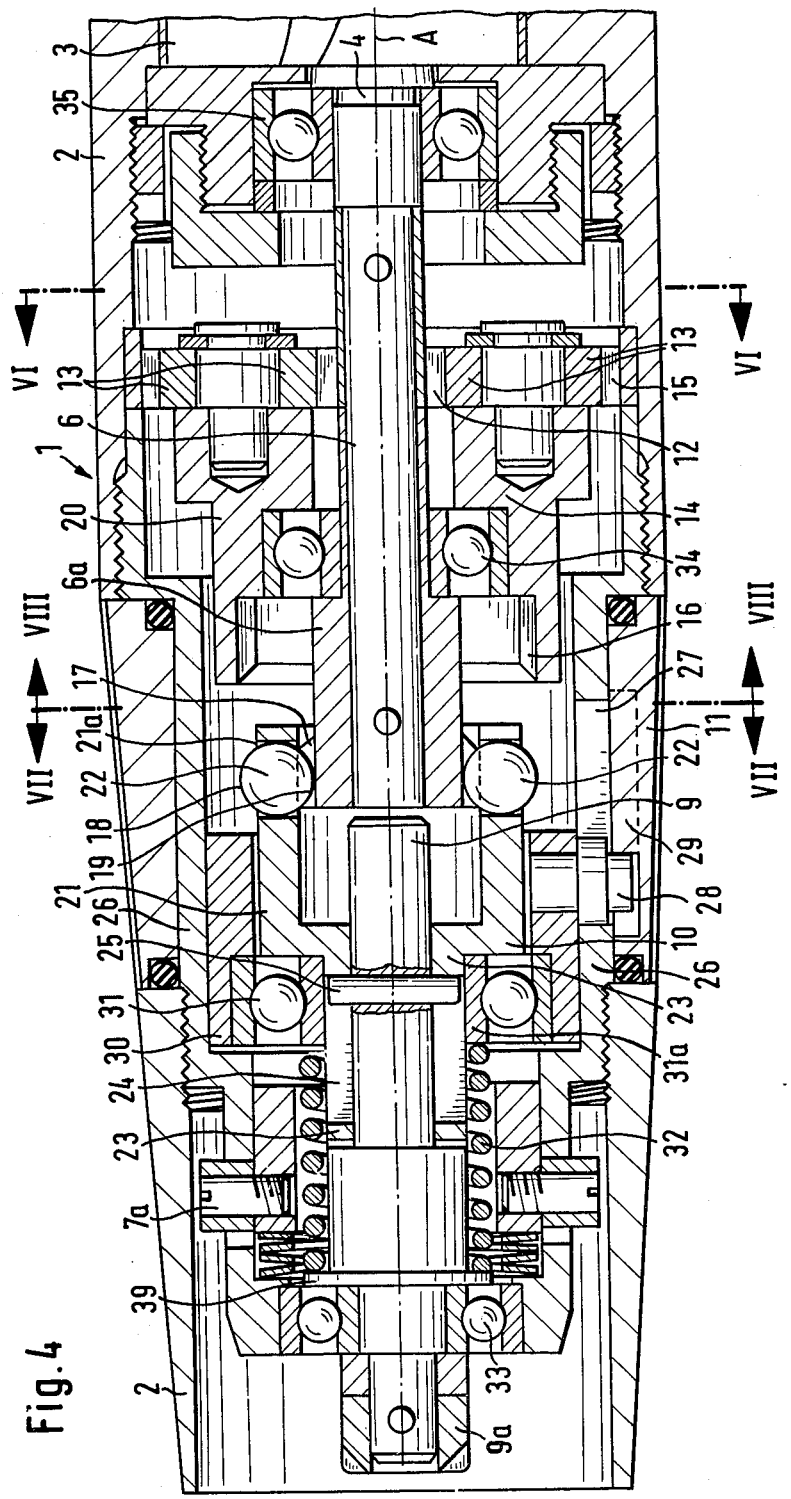
FIG. 4 is a longitudinal sectional view of the dental handpiece of FIG. 1 showing a detail thereof which comprises the input shaft, the planetary drive, the transmission member and the drive shaft. The transmission member is shown directly engaged with the input shaft to provide for a 1:1 transmission ratio.

Referring more particularly to FIG. 1, dental handpiece 1 includes a cylindrical handpiece sleeve 2 and a tip 7 which is adapted to be received within sleeve 2. Handpiece sleeve 2 which comprises a substantially cylindrical sleeve at the right end thereof encloses a drive motor 3, e.g. an electric motor, a planetary gear 5 and a transmission member 10. The handpiece 1 is provided at its right end with a flexible supply tube 3a, in which a current supply line for the drive motor 3 is provided.

Also contained within sleeve 2 is a spur gear 9a connected with an output drive shaft 9 which is directly connected with transmission member 10, and an inner bayonet pin 7a connected with shaft 9.

Tip 7 has means at one end thereof to receive a tooth treatment tool 8 and bayonet slots 7b which are adapted for connection with bayonet pin 7a to connect tip 7 with sleeve 2. Contained within tip 7 is another spur gear 9'a connected with a tip drive shaft 9'. When tip 7 is connected with sleeve 2 by means of the bayonet connectors 7a and 7b, spur gears 9'a and 9a are engaged to connect output and tip drive shafts 9 and 9', respectively, together and tooth treatmnt tool 8 with transmission member 10.

The shaft 4 (see FIGS. 4 and 5) of motor 3 drives the input shaft or drive 6 of planetary gear or drive 5 via a clutch. Shafts 4 and 6 may alternatively be made of one piece.

By means of planetary gear 5, via drive shaft 9, tooth treatment tool 8 inserted in the tip 7 of the handpiece 1 is driven. The tip 7 of the handpiece 1 is straight according to the embodiment of FIG. 1. According to the embodiment of FIG. 2, tip 7 may alternatively be angular. In both the FIG. 1 and FIG. 2 embodiments, handpiece tip 7 has bayonet slots 7b, which are for connection with the handpiece sleeve 2 can be brought into locking engagement with inner bayonet pin 7a of handpiece sleeve 2. To release tip 7 from the handpiece sleeve 2, tip drive shaft 9' is separated from drive shaft 9 by means of spur gears 9'a and 9a. The drive of the tooth treatment tool 8 occurs in several speeds. The different speeds are adjustable by transmission member 10 which can be brought into engagement with planetary gear 5 in different transmission ratios. For this purpose, transmission member 10 is displaceable parallel to the axis A of the handpiece sleeve 2 by means of an external shift member 11 which is designed as a rotary ring.

The planetary drive mechanism includes planetary gear or drive 5 which is one drive control which can be transmitted to transmission member 10 and input shaft or input drive 6 is a second drive control which can be transmitted to transmission member 10.

Figure 5:
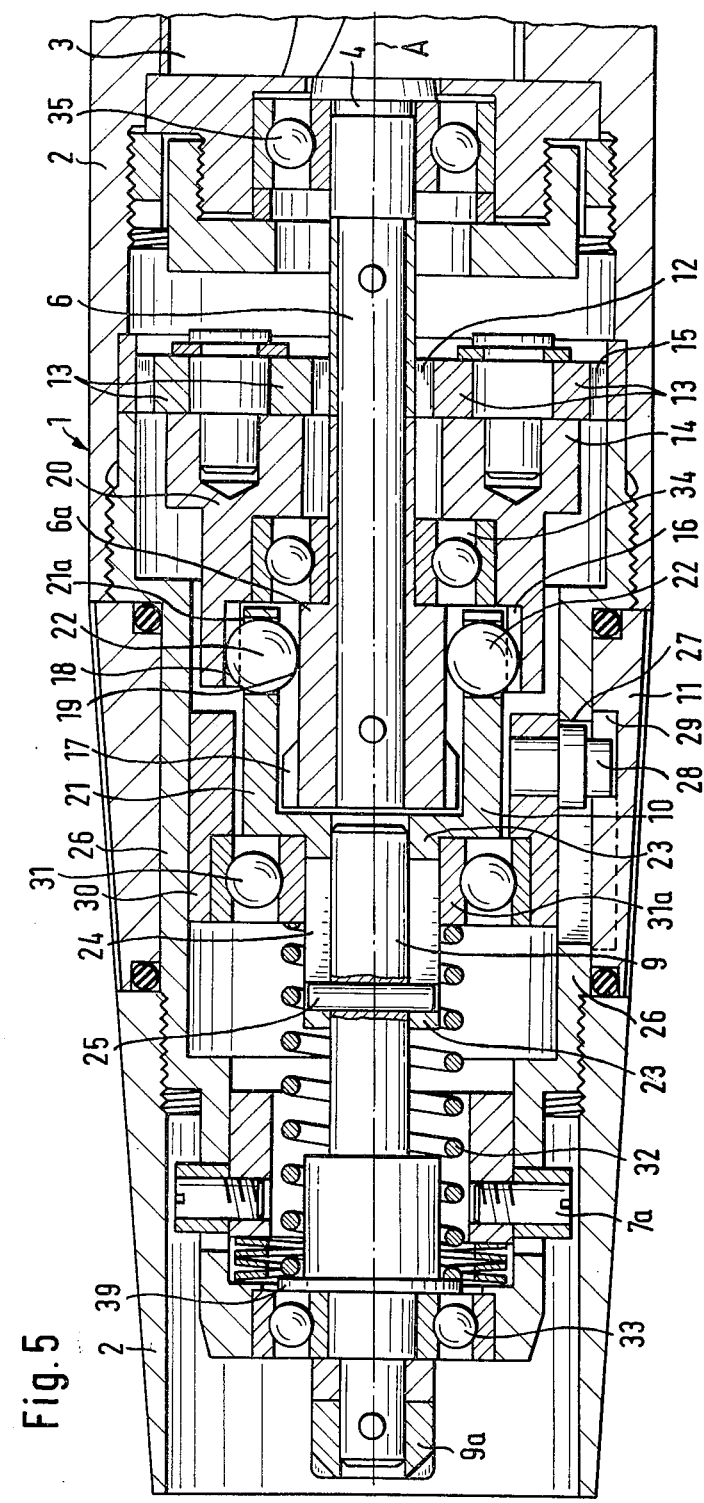
FIG. 5 is a longitudinal section similar to the longitudinal section of FIG. 4, but showing the transmission member directly engaged with a drive stub of the planetary gear to provide for a speed reduction and a step-down transmission ratio to the transmission member.
Figure 6:
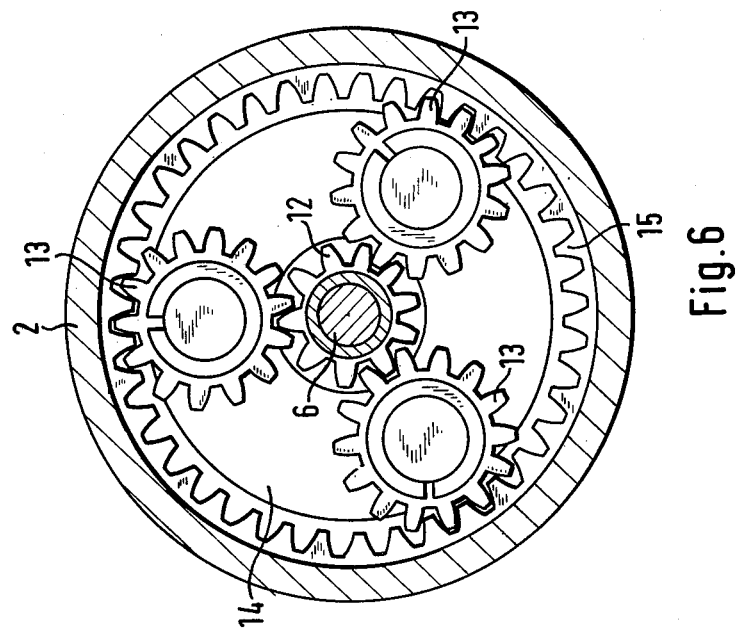
FIG. 6 is a sectional view taken along lines VI—VI of FIG. 4.
Figure 8:
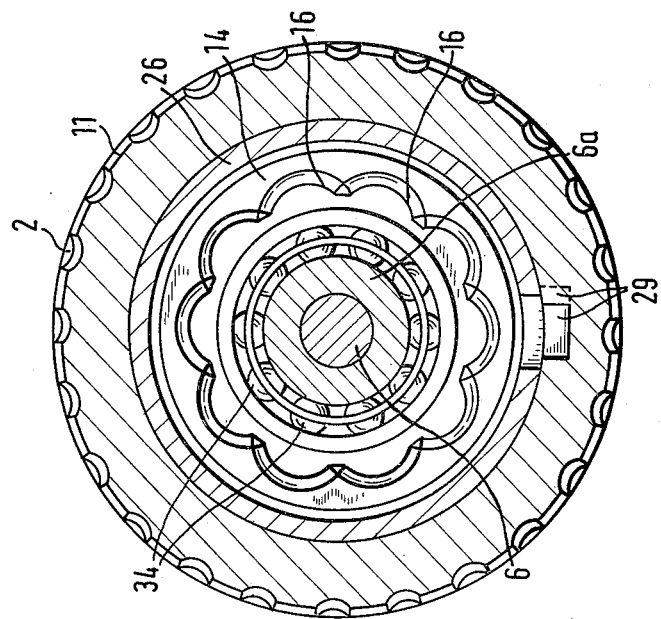
FIG. 8 is a sectional view taken along lines VIII—VIII of FIG. 4.
Figure 7:
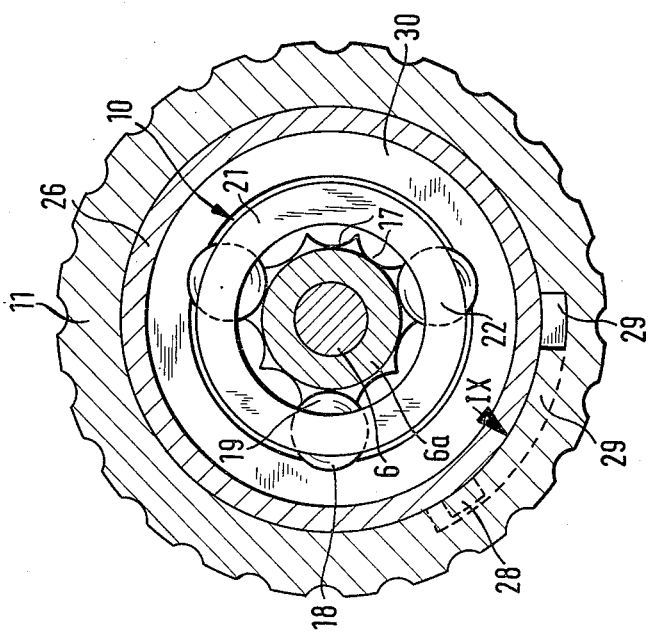
FIG. 7 is a sectional view taken along lines VII—VII of FIG. 4.

Referring now more particularly to FIGS. 4 to 6, planetary drive 5 includes a central roll body or sun gear 12, epicyclic roll bodies or planet gears 13, ring gear or major wheel 15, epicyclic carrier 14 which includes a drive stub 20.

Input drive 6 includes a motor shaft 4 which is connected with input shaft 6. Input drive 6 also includes intermediate sleeve 6a which is fixed to the outer surface of shaft 6 so as to be rotatable therewith and non-movable axially thereof along axis A. Input drive 6 transmits one drive speed to transmission 10 and planetary drive 5 through drive stub 20 transmits another drive speed to transmission 10.

The planetary gear 5 has its gear parts in mutual engagement, and in engagement with central roll body 12 which is designed as a gear wheel and secured on input shaft 6, epicyclic roll bodies 13 designed as epicyclic gear wheel in engagement with the central roll body 12, epicyclic carrier 14 designed as an annular disk carrying epicyclic roll bodies 13, and major wheel 15 in engagement with epicyclic roll bodies 13 and designed as a non-rotational hollow gear rim fixed with sleeve 2. These interengaging gear parts of the planetary gear 5 are arranged axially and radially immobile with reference to axis A of handpiece sleeve 2.

Transmission member 10 includes a circumferential cylindrical wall 21 provided with openings 21a which are adapted to receive and hold balls 22. The diameter of balls 22 is larger than the thickness of wall 21 so that portions 18 and 19 extend beyond wall 21. Portion 18 extends outwardly away from axis A, and portion 19 extends inwardly towards axis A. Transmission member 10 also includes a hollow type trunnion extension 23 connected with wall 21 and extending in the opposite direction. Trunnion extension 23 is axially slidably connected with drive shaft 9 by means of cross pin 25 and is provided with at least one elongated continuous axial slot 24 ending before the free end of the trunnion extension. Cross pin 25 extends through slot 24 and controls and limits the axial movement of trunnion extension 23, and therefore transmission 10 along drive shaft 9. As shown, the two ends of cross pin 25 traverse drive shaft 9 and extend through both slots 24, although one slot 24 would be sufficient.

Engagement means 16,17 are provided on planetary drive 5 and input drive 6, respectively, which are adapted to engage counter-engagement means 18, 19 respectively, formed by the protruding segments on balls 22 of transmission 10, as best seen in FIGS. 4, 5, 7 and 8.

Epicyclic carrier 14 as well as the input shaft 6 of the planetary gear 5 are provided in the region of the end toward the drive shaft 9 with the engagement means 16, 17 which are spaced from each other axially and radially. Engagement means 17 is provided on an intermediate sleeve 6a carried on the input shaft 6. Sleeve 6a is firmly connected with shaft 6. The engagement means 17 is on the outer circumference of intermediate sleeve 6a. The engagement means 16, 17 are selectively engageable with counter-engagement means 18, 19. For this purpose, transmission member 10 is non-rotationally, but axially displaceably arranged on drive shaft 9.

As best seen in FIGS. 4, 5, 7 and 8, engagement means 16 and 17 are formed as axial grooves. Engagement means 16 is distributed and provided on the inner wall of drive stub 20 of the epicyclic carrier 14 and points in the direction of drive shaft 9. Engagement means 17 is on the circumference of the outer wall of and at the free end of intermediate sleeve 6a of input shaft 6. The term axial grooves means that these grooves extend parallel to the axis A of handpiece sleeve 2. The grooves on sleeve 6a face the grooves on drive stub 20, but are spaced from each other.

As is evident in particular from FIGS. 4 and 5, transmission member 10 is designed in the form of an open pot which opens toward input shaft 6. The counter-engagement means 18, 19 are formed by spherical segment-shaped elevations on balls 22 which emerge from both sides of circumferential wall 21 of the pot. Depending on the position of transmission 10, spherical segments 18 engage the engagement means 16 which are formed by the axial grooves of the drive stub 20, or spherical segments 19 engage engagement means 17 formed by the axial grooves of intermediate sleeve 6a. Engagement means 18, 19 are distributed over the inner circumference and over the outer circumference of circumferential wall 21 of transmission member 10. As is further evident from FIGS. 4, 5 and 7, openings 21a are designed in the manner of a cage. Balls 22 which are inserted into openings 21a and which protrude on both sides from circumferential wall 21 provide for ease of engagement with axial grooves 16, 17. The spherical segments which are formed from the protruding portions in turn form counter-engagement means 18, 19 which are free to move with ease into axial grooves 16, 17 and present the same outer surface at all times.

Figure 9:
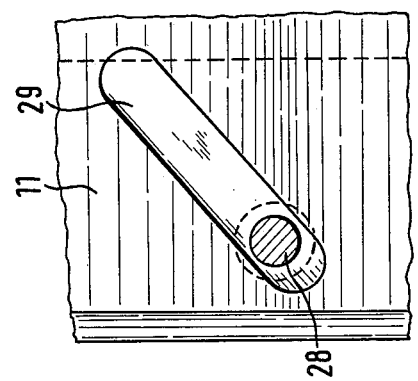
FIG. 9 is a detail of a sectional view in the direction of arrow IX in FIG. 7 and illustrates a detail of the inner wall of the external shift member which is shown as a rotary ring.

Referring now more particularly to FIGS. 4, 5, 7, 8 and 9, handpiece sleeve 2 has an inner sleeve 26 firmly connected with it. Inner sleeve 26 is provided with an oblong hole 27 through which passes a catch pin 28 held fast with the transmission member 10 and extending in a radial direction. External shift member 11, as best seen in FIG. 9, is provided with an oblique groove 29 in its inner wall, and catch pin 28 extends into oblique groove 29. Positioned between inner sleeve 26 and circumferential wall 21 is a bearing sleeve 30. Sleeve 30 surrounds circumferential wall 21 and is spaced from trunnion type extension 23 to provide a space for ball bearing 31 which has its inner bearing ring 31a supported on the outer wall of trunnion 23. Drive shaft 9 is provided with an annular radial projection 39.

A compression spring 32 in the form of a helical spring is provided surrounding hollow-trunnion type extension 23 and is held between inner ring 31a. Upon displacement of transmission member 10 from its FIG. 4 position to the right into its position, spring 39 pushes ball bearings 31 to follow wall 21 and trunnion 23. Drive shaft 9 also has ball bearing 33 and is positioned between shaft 9 and inner sleeve 26. In addition, a ball bearing 34 is provided between the intermediate sleeve 6a and the epicyclic roll body 13. Input shaft 6 has another ball bearing 35.

Handpiece 1 may also be divided into a motor portion and a handpiece portion. FIG. 3 schematically shows the arrangement of the planetary gear 5 when the handpiece 1 is transversely divided into a motor portion 1a and a handpiece portion 1b, and tooth treatment tool 8 is received in handpiece portion 1b. Handpiece portion 1b is provided with an annular groove 37, and motor portion 1b includes a pressure-responsive coupling hook 38 adapted for engagement with annular groove 37 to lock handpiece portion 1b with motor portion 1a for mutual rotation about axis A. A spring 36 is provided to exert pressure on hook 38 and cause it to become released from groove 37 so that portions 1a and 1b can be decoupled. Spring 36 is operable from outside of motor portion 1a.

OPERATION

When shift member 11 is rotated out of the position shown in FIG. 4, catch pin 28 moves to the right into the position shown in FIG. 5. In doing so, catch pin 28 moves transmission member 10 via bearing sleeve 30 and ball bearing 31, so that counter-engagement means 19 move out of engagement means 17, and counter-engagement means 18 come into engagement with the engagement means 16 of epicyclic carrier 14. A change of transmission ratio is thus brought about. In the position shown in FIG. 4, the transmission ratio is 1:1; and, in the position shown in FIG. 5, the transmission ratio is stepped down to a ratio of 5:1.

Within the general concept of the invention, the planetary drive mechanism may be considered to be the input shaft 4 which drives both the planetary gear 5 and the intermediate sleeve 6a. Both the planetary gear 5 and sleeve 6a are connected with input shaft 6 so as to impart different speeds to transmission 10 through the cooperation of the interengaging means 16, 17 with the counter-engaging means 18, 19. The planetary drive mechanism includes one drive through the planetary gear arrangement 5 and another drive through the intermediate sleeve arrangement 6a.

While there has been shown what is considered to be the preferred embodiments of the invention, it will be obvious to those skilled in the art that various changes and modifications may be made therein without departing from the scope of the invention.

I claim:

1. In a dental handpiece adapted to have a tooth treatment tool inserted in the tip thereof to drive the tool at different speeds, an output drive shaft for driving the tool, an elongated sleeve having a central axis, a drive motor in said sleeve, a planetary drive mechanism, an input drive shaft coupling said planetary drive mechanism to said drive motor, a transmission member axially aligned with and engageable with said planetary drive mechanism in different transmission ratios to impart different speeds to the tooth treatment tool, and an external shift member coupled with said transmission member for displacement thereof axially of said handpiece along the central axis, the improvement comprising:

interengaging means on said planetary drive mechanism;
counter-engagement means on said transmission member; and
means coupling said transmission member to said output drive shaft solely for rotation of said output drive shaft with said transmission member but permitting axial displacement of said transmission member along said output drive shaft for engaging said counter-engaging means with said interengaging means in different conditions to impart the different speeds to the tool
said planetary drive mechanism comprising a planetary gear arrangement coupled to said input shaft and an intermediate sleeve coupled to said input shaft;
said planetary gear arrangement including epicyclic roll bodies and a drive stub coupled with said roll bodies, said stub having a circumferential wall facing said intermediate sleeve and coaxial therewith;
said transmission member including a circumferential cylindrical wall coaxial with and opening towards said intermediate sleeve;
said interengaging means including first and second axial slots, said first axial slots being peripherally spaced on and internally of said circumferential wall of said stub, and said second axial slots being peripherally spaced on and over said intermediate sleeve at an end thereof towards said transmission member;
said counter-engaging means including peripherally spaced first segments carried by and extending externally from said cylindrical wall for engagement with said first axial slots, and peripherally spaced second segments carried by and extending internally from said cylindrical wall for engagement with said second axial slots;
said counter-engaging means comprising balls, and a cage structure carried by said cylindrical wall for retaining said balls in said cylindrical wall;
said balls having a diameter greater than the thickness of said wall whereby portions of said balls extend externally and internally of said wall; and,
said externally extending portions forming said first segments and said internally extending portions forming said second segments.

2. A handpiece according to claim 1, wherein:
said transmission member includes a trunnion type extension connected with said cylindrical wall;
said extension having an elongated slot extending through said axial slot to control the axial displacement of said transmission member; and a compression spring surrounding said output drive shaft to urge said counter-engagement means into engagement with said interengagement means upon movement of said external shaft member.

3. In a dental handpiece adapted to have a tooth treatment tool inserted in the tip thereof to drive the tool at different speeds, an output drive shaft for driving the tool, an elongated sleeve having a central axis, a drive motor in said sleeve, a planetary drive mechanism, an input drive shaft coupling said planetary drive mechanism to said drive motor, a transmission member axially aligned with and engageable with said planetary drive mechanism in different transmission ratios to impart different speeds to the tooth treatment tool, and an external shift member coupled with said transmission member for displacement thereof axially of said handpiece along the central axis, the improvement comprising:

interengaging means on said planetary drive mechanism, said interengaging means including interengaging gear parts on said planetary drive mechanism axially and radially fixed against translational movement along the central axis,
counter-engagement means on said transmission member; and, means coupling said transmission member to said output drive shaft solely for rotation of said output drive shaft with said transmission member along said output drive shaft for engaging said counter-engaging means with said interengaging means in different conditions to impart the different speeds to the tool;

said planetary drive mechanism including first and second drives;

said first drive comprising said interengaging gear parts, said interengaging gear parts including a planetary gear arrangement having a central roll body coupled with said input shaft, epicyclic roll bodies and an outer ring gear coupled with said central roll body through said epicyclic roll bodies, and an epicyclic carrier comprising a drive stub and stub circumferential wall coupled with said epicyclic roll bodies;

said second drive means including an intermediate sleeve axially and radially fixed on said input shaft;

said transmission member including a transmission circumferential cylindrical wall coaxial with and opening towards said intermediate sleeve;

said interengaging means including first and second axial slots, said first axial slots being peripherally spaced on and internally of said stub circumferential wall, and said second axial slots being peripherally spaced on and externally of said intermediate sleeve at an end thereof towards said transmission member;

said counter-engaging means including an engagement element having peripherally spaced first segments carried by and extending from said transmission circumferential wall for alternative engagement in one condition of said counter-engaging means with said first axial slots; and peripherally spaced second segments carried by and extending internally from said transmission circumferential wall for engagement with said second axial slots in another alternative condition of said counter-engaging means; and, said counter-engaging means further comprising balls, and a cage structure carried by said cylindrical wall for retaining said balls in said cylindrical wall; said balls having a diameter greater than the thickness of said wall whereby portions of said balls extend externally and internally of said wall; and, said externally extending portions forming said first segments and said internally extending portions forming said second segments.

4. A handpiece according to claim 3, including:

an inner sleeve having an oblong opening;

said external shaft member having an oblong groove;

a catch pin fixedly associated with said transmission member, said catch pin passing through said oblong opening and said oblong groove to move said transmission member upon movement of said external shaft member.

5. A handpiece according to claim 4, said handpiece including:

a separate motor portion and a separate handpiece portion; and, cooperative catch means on said motor portion and said handpiece portion to facilitate connection and disconnection thereof.

* * * * *